United States Patent [19]

Li

[11] Patent Number: 5,406,851
[45] Date of Patent: Apr. 18, 1995

[54] ULTRASONIC TRANSDUCER SYSTEM

[75] Inventor: Yan Li, San Diego, Calif.

[73] Assignee: XXSYS Technologies, Inc., San Diego, Calif.

[21] Appl. No.: 100,734

[22] Filed: Aug. 2, 1993

[51] Int. Cl.6 ........................................... G01N 29/28
[52] U.S. Cl. .................................................... 73/644
[58] Field of Search .......................... 73/632, 642, 644

[56] References Cited

U.S. PATENT DOCUMENTS

| | | | |
|---|---|---|---|
| 3,760,634 | 9/1973 | Birks | 73/644 |
| 3,921,442 | 11/1975 | Soloway | 73/644 |
| 4,703,656 | 11/1987 | Bhardwaj | 73/644 |
| 5,121,628 | 6/1992 | Merkl et al. | 73/632 |

Primary Examiner—Hezron E. Williams
Assistant Examiner—Rose M. Finley
Attorney, Agent, or Firm—Gregory Garmong

[57] ABSTRACT

An ultrasonic transducer system includes a transducer coupler body made of a material that transmits ultrasonic waves therethrough and an ultrasonic transducer joined to a first portion of the transducer coupler body. A footprint face plate is joined to a second portion of the transducer coupler body. The first portion and the second portion are selected such that an ultrasonic wave can propagate therebetween through the transducer coupler body. The footprint face plate extends beyond the transducer coupler body and has a footprint contact face on one end thereof, with the width of the contact face being much smaller than its length.

16 Claims, 2 Drawing Sheets

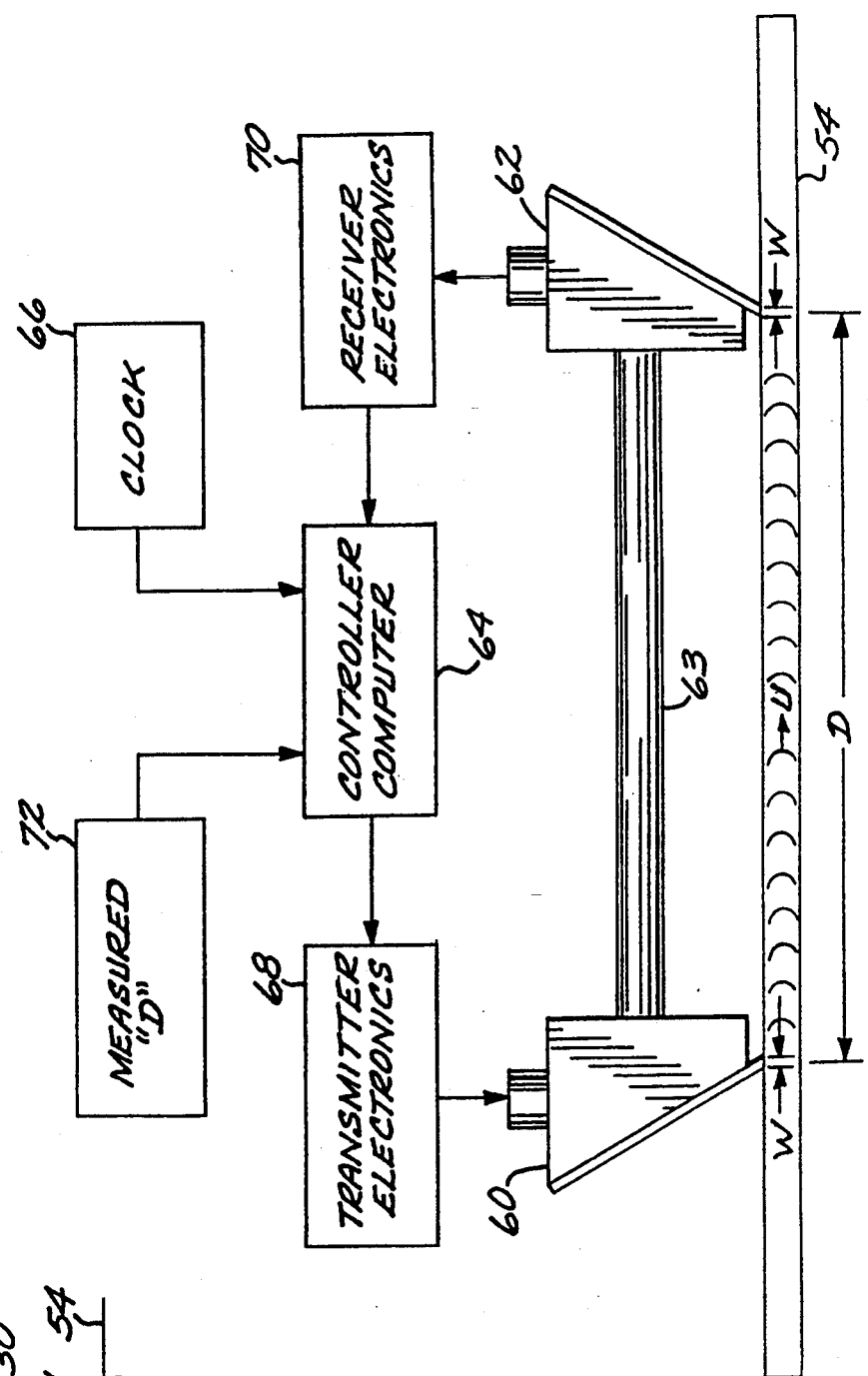
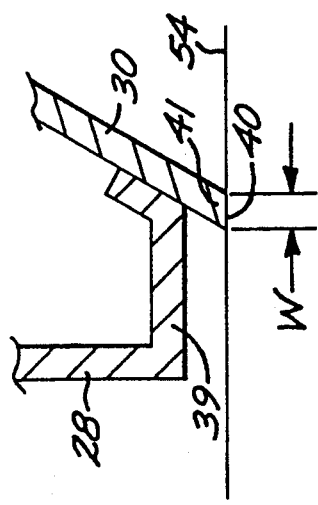

ULTRASONIC TRANSDUCER SYSTEM

BACKGROUND OF THE INVENTION

This invention relates to ultrasonic transducers, and, more particularly, to a system for generating and coupling various types of ultrasonic waves with a surface of a workpiece.

An ultrasonic transducer is a device that interconverts electrical and mechanical waves. For example, a 1 megahertz (one million cycles per second) electrical signal fed to such a transducer produces a 1 megahertz mechanical output signal. Conversely, a mechanical signal fed to an ultrasonic transducer produces an electrical output signal. The ultrasonic transducer can therefore be used to produce mechanical waves that are coupled into a workpiece, and/or receive the mechanical waves propagated through the workpiece or along the surface of the workpiece. In either case, the mechanical waves are interconverted with electrical signals that are more readily controlled and/or processed by external electrical circuitry.

In some conventional situations the ultrasonic transducer signal is readily and precisely coupled with the workpiece. For example, if the workpiece is a solid piece of relatively large diameter and the ultrasonic waves of interest are bulk waves that travel through the interior of the solid piece, a transmitting ultrasonic transducer can be placed on one end of the solid piece and a receiving ultrasonic transducer can be placed on the opposite end. The distance of travel between the transmitting and receiving transducers is the distance between the ends of the workpiece.

In other situations coupling between the ultrasonic transducer and the workpiece is not so readily accomplished, nor is the effective propagation distance of the ultrasonic wave so well defined. Where the workpiece is a thin sheet of material, the ultrasonic transducers are placed flat against the surface of the sheet. Since the ultrasonic transducers have a contact area dimension parallel to the direction of propagation, the distance of ultrasonic wave propagation through the sheet is not well defined. Calibration techniques may be used in some cases, but are not practical in others. The same problem arises for complexly shaped workpieces.

An alternative approach is to place the workpiece into a tank of a liquid couplant material. Ultrasonic transducers spaced apart from the workpiece couple with the workpiece through the liquid couplant material. Even with this configuration, propagation distances are also difficult to determine precisely.

There is a need for an approach to introducing ultrasonic waves into thin sheets, plates, and complexly configured workpieces, and receiving them from such workpieces, at precisely defined locations. The technique should be operable with various types of ultrasonic waves. The present invention fulfills this need, and further provides related advantages.

SUMMARY OF THE INVENTION

The present invention provides an ultrasonic transducer system useful in introducing ultrasonic waves into a workpiece and receiving ultrasonic waves from a workpiece, at precisely defined locations on the surface of the workpiece. The workpiece is not immersed in a fluid, and remains completely dry except where a thin film of couplant is used between the ultrasonic transducer system and the workpiece. The system is readily constructed and can be used with a wide range of types of ultrasonic transducers.

In accordance with the invention, an ultrasonic transducer system comprises a transducer coupler body made of a material that transmits ultrasonic waves therethrough and an ultrasonic transducer joined to a first portion of the transducer coupler body. A footprint face plate is joined to a second portion of the transducer coupler body. The first portion and the second portion are selected such that an ultrasonic wave can propagate therebetween through the transducer coupler body. The footprint face plate comprises a material that transmits ultrasonic waves therethrough. The footprint face plate extends beyond the transducer coupler body and has a footprint contact face on one end thereof. The width of the footprint contact face is preferably much less than its length, to define a narrow strip for transmission or receipt of an ultrasonic signal.

In another embodiment, an ultrasonic transducer system comprises a transducer coupler body made of a material that transmits ultrasonic waves therethrough, and an ultrasonic transducer joined to a first portion of the transducer coupler body and positioned to direct an ultrasonic wave into the transducer coupler body. A footprint face plate is joined to a second portion of the transducer coupler body. The first portion and the second portion are selected such that at least a portion of the footprint face plate is impinged upon by an ultrasonic wave propagated by the ultrasonic transducer at an angle of greater than zero but less than ninety degrees. The footprint face plate comprises a material that transmits ultrasonic waves therethrough. The footprint face plate extends beyond the transducer coupler body and has a footprint contact face on one end thereof.

More generally, an ultrasonic transducer system operable to transceive ultrasonic signals relative to a surface comprises an ultrasonic transducer operable to transceive an ultrasonic signal along a transceiving path, and a footprint face plate oriented at an angle of more than zero and less than ninety degrees to the transceiving path. The footprint face plate has a contact face at one end thereof that is oriented at an angle of more than zero and less than ninety degrees to a plane of the footprint face plate adjacent to the contact face. The system further includes medium means for propagating an ultrasonic wave along the transceiving path between the ultrasonic transducer and the footprint face plate.

In the approach of the invention, the transducer propagates a first ultrasonic wave into the transducer coupler body. The first ultrasonic wave impinges upon the footprint face plate. A second ultrasonic wave propagates through the footprint face plate to the footprint contact face. A third ultrasonic wave propagates from the contact face into and through the workpiece against which the footprint face plate is pressed. The receipt of an ultrasonic wave occurs by the reverse path.

The footprint face plate is desirably of narrow width, and of much larger length. The third ultrasonic wave is propagated in the workpiece parallel to the narrow width direction of the footprint contact face. The ultrasonic wave in the workpiece effectively emanates from a narrow strip source. Thus, it is possible to determine with great accuracy the distance of travel of the ultrasonic wave between the transmitting transducer coupler and the receiving transducer coupler. Lamb waves can be readily transmitted and received by this approach, for example.

The present invention provides an important advance in the art. Ultrasonic waves of varying types can be produced and coupled into or out of thin sheets and other objects whose edges are not accessible for attachment of an ultrasonic transducer. The ultrasonic coupler with a strip-like footprint face plate permits the location of the point of transmission or receipt of the ultrasonic wave in the workpiece to be established precisely. Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 3 is an enlargement of a detail of FIG. 2; and

FIG. 4 is a side elevational view of transmitting and receiving ultrasonic transducer systems used with a sheet workpiece, with a schematic depiction of the control system and associated electronics.

DETAILED DESCRIPTION OF THE INVENTION

FIGS. 1-8 depict an ultrasonic transducer system 20 according to the invention. The ultrasonic transducer system 20 includes a transducer coupler body 22 with an ultrasonic transducer 24 affixed to one of the faces of the transducer coupler body and communicating with the interior of the transducer coupler body 22.

Figure 1:
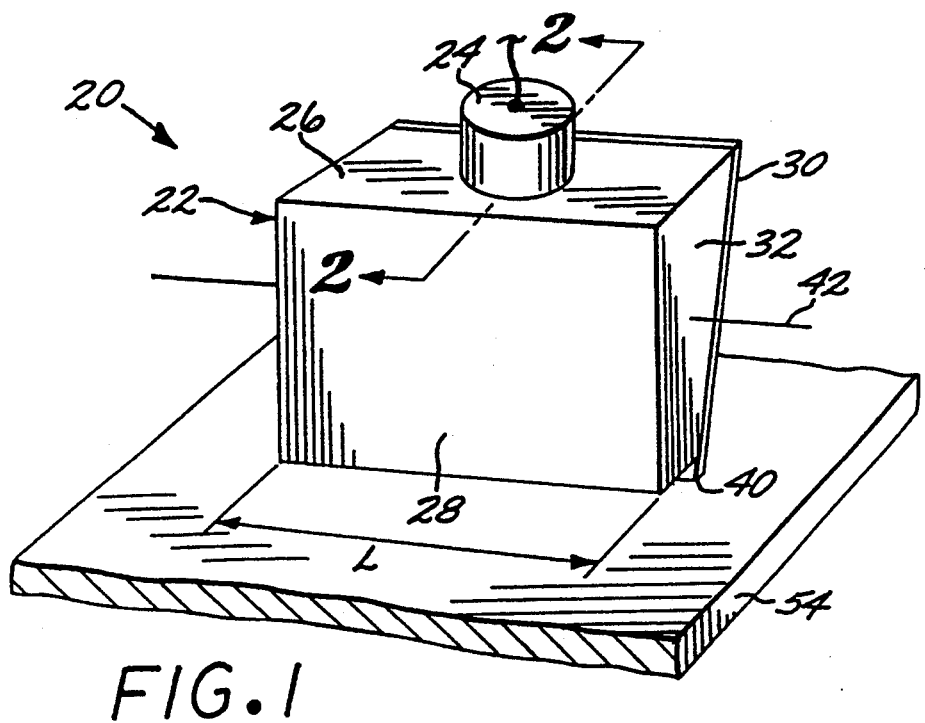
FIG. 1 is a perspective view of an ultrasonic transducer system.
Figure 2:
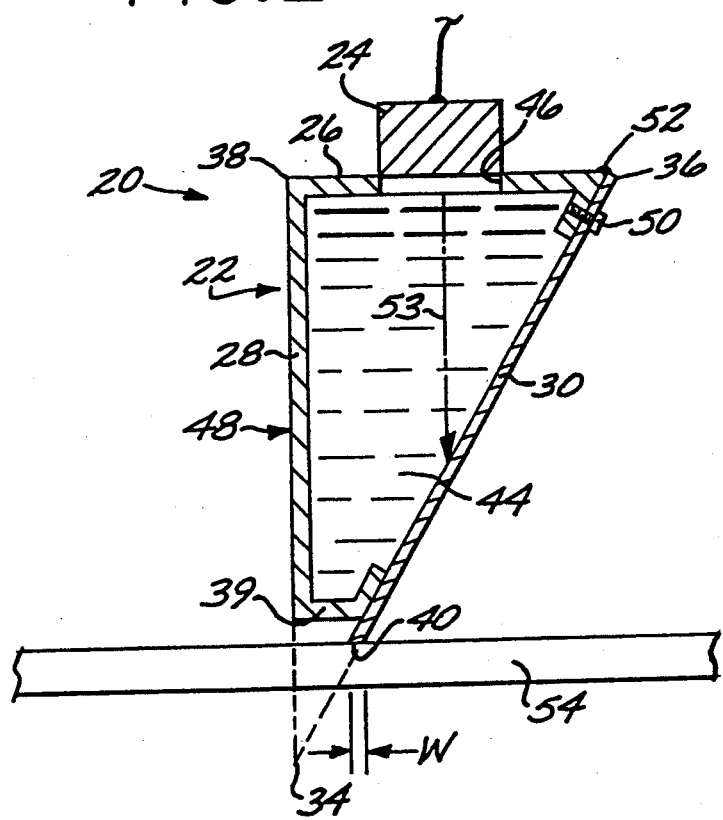
FIG. 2 is a side sectional view of the ultrasonic transducer system of FIG. 1, taken along lines 2—2.

The transducer coupler body 22 includes three rectangular face plates 26, 28, and 30 that extend between two opposing and separated base plates 32. The three face plates 26, 28, and 30 are perpendicular to the base plates 32, forming a right prism. As shown in FIG. 2, the face plates 26, 28, and 30 lie in a generally triangular pattern when viewed in section perpendicular to the prism axis, with the angle between the face plates 26 and 28 being 90 degrees in the preferred embodiment. There are therefore three vertices 34, 35, and 38 of the triangular arrangement. The first face plate 26 and the second face plate 28 are joined at vertex 88 at an angle of 90 degrees, as mentioned. The first face plate 26 and the third face plate 30 are joined at vertex 36.

The second face plate 28 and the third face plate 30 are not joined at the vertex 34. Instead, the triangle is truncated adjacent to the vertex 34, with a truncation plate 39 extending between the second face plate 28 and the third face plate 30. The truncation plate 39 is preferably parallel to the first face plate 26.

The third face plate 30, also termed the inclined face plate or footprint face plate, extends beyond the remainder of the transducer coupler body 22. A footprint contact face 40 is at the end of the footprint face plate 30 which extends beyond the transducer coupler body 22. The footprint contact face 40 is typically flat to contact a surface of a workpiece, but may be curved if desired.

Thus, the face plates 25, 28, and 90, the truncation plate 39, and the two base plates 32 together form a right prismatic solid body, which is substantially a right triangular prismatic body with the face plates 26, 28, 30, and 39 parallel to a prism axis 42, and the base plates 32 perpendicular to the prism axis 42. (More precisely, the body is a quadrilateral prism, but the short length of the truncation plate 39 results in a substantially triangular appearance.)

In the preferred embodiment, the face plates 26, 28, 30, and 39, and the base plates 32 are sealed together to form a sealed hollow body. An interior 44 of the hollow body is filled with a fluid couplant, preferably water. The ultrasonic transducer 24 is preferably affixed to the first face plate 26 by providing a threaded bore 46 in the first face plate 26 and threads on the exterior of the body of the transducer 24. The transducer 24 is threaded into the bore 46 during assembly. The interior 44 is filled with a fluid such as water before the ultrasonic transducer 24 is threaded into the first face plate 26.

In the preferred construction, the first face plate 26 (also termed the transducer support face plate), the second face plate 28 (also termed the closure face plate), the truncation plate 39, and the base plates 32 are machined as a single integral body 48. The footprint or third face plate 30 is provided as a separate plate. The integral body 48 is preferably formed of aluminum (including aluminum and aluminum alloys) and the footprint face plate 30 is preferably formed of stainless steel or copper (including copper and copper alloys), most preferably brass. The footprint face plate 90 is fastened to the integral body 48 by any appropriate means, preferably fasteners 50, and sealed with a sealant such as a wax bead 52.

In operation, the ultrasonic transducer 24 produces a first ultrasonic signal that is transmitted through the fluid within the interior 44 of the transducer coupler body 22 along a transceiving path 59 between the ultrasonic transducer and the footprint face plate. The first ultrasonic signal excites a second ultrasonic signal in the footprint face plate 30. The second ultrasonic signal in the footprint face plate 30 excites a third ultrasonic signal in a workpiece 54.

The preceding discussion has emphasized the ultrasonic waves that can be produced and transmitted using the ultrasonic transducer system 20. The same respective geometries are used to receive the same ultrasonic waves.

FIG. 4 illustrates the use of the ultrasonic transducer system 20 in performing a measurement of ultrasonic wave velocity in the workpiece 54. The ultrasonic transducer system 20 can be used in other configurations for other applications and measurements, but the approach of FIG. 4 will illustrate the system and its advantages.

A first ultrasonic transducer system 60 transmits an ultrasonic wave U along the length of the workpiece 54. A second ultrasonic transducer system 62 receives the ultrasonic wave U after it has passed along the length of the workpiece 54. Each of the ultrasonic transducer systems 60 and 62 has a physical configuration operable in much the same manner as just described, but different in some configurational aspects. For example, the ultrasonic transducer systems 60 and 62 have a generally rectangular cross section cut on one side by the footprint face plate, rather than a substantially triangular cross section. Also, the transducer coupler bodies of the transducer systems 60 and 62 are solid rather than hollow.

The distance D over which the ultrasonic wave propagates from the ultrasonic transducer system 60 to the ultrasonic transducer system 52 is measured and is known with excellent certainty. Referring back to FIG. 2, the width W of the footprint face plate 40 can be made quite small compared with the length L of the footprint face plate (FIG. 1), and is preferably about 0.020 inch or less. Therefore the uncertainty in the value of D, due to uncertainty in the effective position or transmission or receipt of the wave U, is also quite small. This characteristic distinguishes the present approach from conventional wedge transducers, where there is a large surface area from which the acoustic is propagated or where it is received. It is difficult to determine the effective propagation distance precisely in this approach. In the present approach, a handle 62 may be optionally provided to position the transducer systems 60 and 62 at the desired spacing.

The time required to propagate the wave W from ultrasonic transducer system 60 to ultrasonic transducer system 62 is determined by electronic apparatus depicted in FIG. 4. A controller 64, which is typically a microcomputer, receives clock pulses from a clock 66. The controller 64 instructs a transmitter electronics 66 to initiate an appropriate electrical waveform to the transducer of the transmitter ultrasonic transducer system 62. The time of sending the pulse is known from the clock 66.

The electrical signal corresponding to the received ultrasonic wave is provided from the receiving ultrasonic transducer 62 to receiver electronics 70. The received electrical waveform is analyzed and compared to the transmitted electrical waveform to ensure that the corresponding parts of the signals are compared. When a match is made, the time of receipt of that portion of the ultrasonic wave is determined by the controller 54 by comparison with the clock signal 55. The difference is the time of flight t of the ultrasonic wave U over the measured distance D, numeral 72. The velocity of the ultrasonic wave U through the workpiece 54 is determined as distance D divided by the time of flight t.

As indicated, this example illustrates the use of the ultrasonic transducer system 20, but is not to be taken as limiting of its applications.

FIG. 4 shows a flat workpiece 54. The workpiece 54 could also have irregular shapes, such as, for example, a disk. The velocity of ultrasound around the circumference of a disk is of interest in some inspection techniques. It is quite difficult to make such a determination using a conventional ultrasonic transducer arrangement, because of problems in knowing the distance D accurately and in achieving coupling to the disk circumference with a generally circular transducer face. The present approach overcomes both of these problems. Because the width W of the footprint contact face 40 is small, the uncertainty in D is small. Because the footprint contact face 40 of the ultrasonic transducer system 20 is in the form of a long, narrow rectangle, it is readily placed against the circumference of the disk with the long direction of the rectangle parallel to the disk axis. Good coupling into and out of the disk circumference is thereby achieved without using of a couplant applied to the disk surface, in many cases. In cases where a hard surface is being studied with the system 20, it may be necessary to place a thin-film of a couplant between the footprint contact face 40 and the workpiece 54.

The present approach provides an ultrasonic transducer system that produces ultrasonic wave propagation Information of good accuracy. Coupling is excellent, and a variety of different types of ultrasonic waves can be generated, propagated, and received. Although a particular embodiment of the invention has been described in detail for purposes of illustration, various modifications may be made without departing from the spirit and scope of the invention. Accordingly, the invention is not to be limited except as by the appended claims.

What is claimed is:

1. An ultrasonic transducer system, comprising:
   a transducer coupler body made of a material that transmits ultrasonic waves therethrough;
   an ultrasonic transducer joined to a first portion of the transducer coupler body; and
   a footprint face plate joined to a second portion of the transducer coupler body, the first portion and the second portion being selected such that an ultrasonic wave can propagate therebetween through the transducer coupler body, the footprint face plate comprising a material that transmits ultrasonic waves therethrough, the footprint face plate extending beyond the transducer coupler body and having a footprint contact face on one end thereof.

2. The transducer system of claim 1, wherein the transducer coupler body has opposing parallel bases.

3. The transducer system of claim 1, wherein the interior of the transducer coupler body is hollow.

4. The transducer system of claim 3, further including a liquid filling the hollow interior of the transducer coupler body.

5. The transducer system of claim 4, wherein the liquid is water.

6. The transducer system of claim 1, wherein the interior of the transducer coupler body is solid.

7. The transducer system of claim 1, wherein the transducer coupler body has the shape of a substantially right triangular, right prismatic body, with the face plate joined to a hypotenuse of the right triangular body.

8. The transducer system of claim 1, wherein the transducer coupler body has the shape of a quadrilateral right prismatic body with two opposing faces of the quadrilateral parallel to each other, and wherein the face plate is joined to a first non-parallel side and the transducer to a second non-parallel side of the transducer coupler body.

9. The transducer system of claim 1, wherein the footprint face plate is formed of a metal.

10. The transducer system of claim 1, wherein the footprint face plate is formed of a metal selected from the group consisting of copper and stainless steel.

11. The transducer system of claim 1, wherein the footprint contact face is flat.

12. The transducer system of claim 1, wherein the footprint contact face has a width and a length, and the width is much smaller than the length.

13. An ultrasonic transducer system, comprising:
   a transducer coupler body made of a material that transmits ultrasonic waves therethrough;
   an ultrasonic transducer joined to a first portion of the transducer coupler body and positioned to direct an ultrasonic wave into the transducer coupler body; and
   a footprint face plate joined to a second portion of the transducer coupler body, the first portion and the second portion being selected such that at least a portion of the footprint face plate is impinged upon by an ultrasonic wave propagated by the ultrasonic transducer at an angle of greater than zero but less than ninety degrees, the footprint face plate comprising a material that transmits ultrasonic waves therethrough, the footprint face plate extending beyond the transducer coupler body and having a footprint contact face on one end thereof.

14. An ultrasonic transducer system operable to transceive ultrasonic signals relative to a surface, comprising:
   an ultrasonic transducer operable to transceive an ultrasonic signal along a transceiving path;
   a footprint face plate oriented at an angle of more than zero and less than ninety degrees to the transceiving path, the footprint face plate having a contact face at one end thereof that is oriented at an angle of more than zero and less than ninety degrees to a plane of the footprint face plate adjacent to the contact face; and
   medium means for propagating an ultrasonic wave along the transceiving path between the ultrasonic transducer and the footprint face plate.

15. The transducer system of claim 14, wherein the medium means defines a straight-line transceiving path.

16. The transducer system of claim 14, wherein the medium means comprises a transducer coupler body.

* * * * *